(12) United States Patent
Kleinekofort

(10) Patent No.: US 9,878,086 B2
(45) Date of Patent: Jan. 30, 2018

(54) METHOD AND DEVICE FOR MONITORING AN EXTRACORPOREAL BLOOD CIRCUIT

(75) Inventor: Wolfgang Kleinekofort, Kelkheim (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 570 days.

(21) Appl. No.: 12/373,818

(22) PCT Filed: Jul. 11, 2007

(86) PCT No.: PCT/EP2007/006140
§ 371 (c)(1),
(2), (4) Date: Jan. 14, 2009

(87) PCT Pub. No.: WO2008/006559
PCT Pub. Date: Jan. 17, 2008

(65) Prior Publication Data
US 2009/0292236 A1 Nov. 26, 2009

(30) Foreign Application Priority Data
Jul. 14, 2006 (DE) .......................... 10 2006 032 815

(51) Int. Cl.
*A61M 37/00* (2006.01)
*A61M 1/36* (2006.01)
(52) U.S. Cl.
CPC ........ *A61M 1/3639* (2013.01); *A61M 1/3653* (2013.01); *A61M 1/3656* (2014.02); *A61M 1/3661* (2014.02)
(58) Field of Classification Search
CPC .............. A61M 1/3656; A61M 1/3639; A61M 1/3661; A61M 1/3653
(Continued)

(56) References Cited

U.S. PATENT DOCUMENTS 5,368,555 A * 11/1994 Sussman ............. A61M 1/3472
435/1.1
6,221,040 B1 * 4/2001 Kleinekofort ................... 604/65
(Continued)

FOREIGN PATENT DOCUMENTS

CN 1751749 A 3/2006
DE 37 20 664 A1 1/1989
(Continued)

OTHER PUBLICATIONS

International Preliminary Report on Patentability for PCT/EP2007/006140, dated Jan. 20, 2009.
(Continued)

*Primary Examiner* — Ariana Zimbouski
(74) *Attorney, Agent, or Firm* — Kilyk & Bowersox, P.L.L.C.

(57) ABSTRACT

To monitor an extracorporeal blood circuit during extracorporeal blood treatment, the arterial pressure and venous pressure in the arterial branch and venous branch of the extracorporeal circuit are measured by pressure sensors, and the sum $P_s$ and the difference $\Delta P$ of the arterial pressure and/or venous pressure measured at the same time are calculated. A possible error state is indicated when the sum $P_s$ and/or difference $\Delta P$ lie outside predetermined limit value windows A and B. To reduce the susceptibility to error, a check is preferably also made to ascertain whether the two above conditions are satisfied for n successive measurements.

5 Claims, 3 Drawing Sheets

(58) Field of Classification Search
USPC .................................................. 604/4.01, 65
See application file for complete search history.

(56) References Cited

U.S. PATENT DOCUMENTS

| | | | |
|---|---|---|---|
| 6,384,323 B2 | 5/2002 | Elm et al. | |
| 6,585,763 B1 * | 7/2003 | Keilman | A61B 5/0031 |
| | | | 604/891.1 |
| 6,595,942 B2 * | 7/2003 | Kleinekofort | 604/4.01 |
| 6,767,333 B1 | 7/2004 | Mueller et al. | |
| 6,827,698 B1 * | 12/2004 | Kleinekofort | A61M 1/3658 |
| | | | 210/645 |
| 7,172,569 B2 * | 2/2007 | Kleinekofort | 604/6.06 |
| 7,172,570 B2 * | 2/2007 | Cavalcanti et al. | 604/6.11 |
| 2001/0007930 A1 | 7/2001 | Kleinekofort | |
| 2002/0085952 A1 * | 7/2002 | Ellingboe | A61M 1/3621 |
| | | | 422/45 |
| 2002/0190863 A1 | 12/2002 | Lynn | |
| 2004/0171977 A1 * | 9/2004 | Paolini | A61M 1/3639 |
| | | | 604/4.01 |
| 2004/0217056 A1 * | 11/2004 | Muller et al. | 210/645 |
| 2005/0065459 A1 | 3/2005 | Zhang et al. | |

FOREIGN PATENT DOCUMENTS

| | | |
|---|---|---|
| DE | 101 59 620 C1 | 8/2003 |
| EP | 1 584 339 A | 10/2005 |
| JP | 2000 140101 A | 5/2000 |
| JP | 2001 87379 A | 4/2001 |
| JP | 03 193 059 B2 | 7/2001 |
| WO | 03/002174 A1 | 1/2003 |
| WO | 03/074109 A1 | 9/2003 |
| WO | WO2004/074966 * | 9/2004 |

OTHER PUBLICATIONS

International Search Report, PCT/EP2007/006140, dated Nov. 7, 2007.

Wiklund et al., "Postanaesthesia monitoring revisited: Frequency of true and false alarms from different monitoring devices," J. Clinical Anesthesia 1994, 6: 182-188.

* cited by examiner

| Cause of false alarms | PA | PV | $P_s$ | $\Delta P$ |
|---|---|---|---|---|
| Positional change of patient, upwards | ↑ | ↑ | ↑ | → |
| Positional change of patient, downwards | ↓ | ↓ | ↓ | → |
| Decrease in patient's blood pressure | ↓ | ↓ | ↓ | → |
| Increase in patient's blood pressure | ↑ | ↑ | ↑ | → |
| Increase in viscosity of blood through ultrafiltration | ↓ | ↑ | → | ↑ |
| Decrease in viscosity of blood through infusions and refilling | ↑ | ↓ | → | ↓ |

METHOD AND DEVICE FOR MONITORING AN EXTRACORPOREAL BLOOD CIRCUIT

CROSS REFERENCE TO RELATED APPLICATIONS

This is a 371 national phase application of PCT/EP2007/006140 filed Jul. 11, 2007, claiming priority to German Patent Application No. 10 2006 032 815.9 filed Jul. 14, 2006.

FIELD OF INVENTION

The present invention relates to a method for monitoring an extracorporeal blood circuit during extracorporeal blood treatment, in particular during chronic blood purification therapy, for example during hemodialysis, hemofiltration or hemodiafiltration, and to a device for extracorporeal blood treatment, in particular for hemodialysis, hemofiltration or hemodiafiltration, with a means for monitoring the extracorporeal blood circuit.

BACKGROUND OF THE INVENTION

In the known methods of chronic blood purification therapy such as hemodialysis, hemofiltration or hemodiafiltration, the patient's blood is passed through an extracorporeal blood circuit which is generally equipped with a safety system that permanently monitors the arterial pressure and venous pressure within the circuit. The purpose of monitoring the pressure is to detect various complications that may arise during the extracorporeal blood treatment. Possible treatment complications include: an incorrect vascular access, which may be attributable for example to disconnection of the cannula or to suctioning of the cannula; loss of blood due to the cannula slipping out or due to leakage; kinking of the blood conduit, or coagulation in the blood conduit.

If an error state is detected in the extracorporeal circuit, the known safety systems are generally designed to stop the blood pump, to close the tube clamp in the venous blood conduit and to trigger an acoustic and/or optical warning signal. In this way, the blood treatment device is brought into a state which is safe for the patient, but which nevertheless leads to interruption of the therapy.

Various alarm systems are known with which error states in the extracorporeal blood circuit can be detected. The alarm systems are generally based on monitoring the pressure in the arterial and venous branches of the extracorporeal circuit. The known alarm systems infer the existence of an error state when predetermined limit values are exceeded or fallen below. In general, the decision concerning the error state depends only on whether the actually measured pressure does or does not lie within a predefined range.

The alarm systems based on pressure measurement generally respond when the arterial and/or venous pressure in the extracorporeal circuit exceeds or falls below a threshold value that can be varied by the hospital personnel between ±20 and ±60 torr. Alarm systems comparing the pressure values with threshold values have the advantage of being able to be rapidly adjusted. In the known systems, the pressure limit values above or below which an alarm is triggered can generally be input manually. These limit values are dependent both on the patient and on the type of treatment and are individually set at the start of each treatment.

With a large threshold range, there is of course the advantage of a low rate of false alarms, but large threshold ranges lead to a time delay between the detection of a patient-critical state and the response of the alarm system. There is additionally the danger of a patient-critical state no longer being able to be safely detected. By contrast, although a small threshold range increases patient safety, it necessarily leads to an increased rate of false alarms, and this can lead to desensitization of the monitoring personnel or even to manual deactivation of the alarm. The known alarm systems that monitor whether a threshold value is fallen below or exceeded have a rate of false alarms of 70-99.5% depending on the physiological parameter that is to be monitored (Wiklund L, Hök B, Stähl K, Jordeby-Jönsson A. Postanaesthesia monitoring revisited: Frequency of true and false alarms from different monitoring devices. J. Clin. Anesth. 1994; 6: 182-188).

The main causes of pressure-induced false alarms are, for example, movements of the patient, fluctuations in the patient's blood pressure, and fluctuations in the viscosity of the patient's blood.

If the patient changes his vertical position, for example if the patient's position is raised or lowered, the extracorporeal pressure rises or falls by about 0.75 torr per cm of height increase or decrease. This effect leads, for example, to the arterial and venous pressure dropping by about 10-20 torr if a patient moves from a seated position to a sleeping position. Since there is a height difference between puncture site and heart in a seated position, the fistula pressure when seated is higher than when lying down.

During night-time dialysis sessions, in particular in home dialysis, pressure-induced false alarms occur mostly when the patient enters the phase of deep sleep. The drop in blood pressure induced by deep sleep leads to a reduction in the pressure in the entire vascular access. By way of the arterial and venous dialysis cannulas, the drop in blood pressure leads to a symmetrical reduction in the arterial pressure and venous pressure in the extracorporeal circuit. Correspondingly, a rise in blood pressure leads to an increase in the arterial pressure and venous pressure.

Fluctuations in the viscosity of the patient's blood generally occur when, during the blood treatment, water is withdrawn from the patient by what is called ultrafiltration. By contrast, when the ultrafiltration rate is reduced, the viscosity of the patient's blood drops, since tissue water and cell water passes from the extracellular and intracellular volume into the blood volume.

In order to avoid false alarms caused by changes in the viscosity of the patient's blood, it is known to use adaptive drift detection algorithms which at fixed time intervals center the alarm limits arranged around the actual arterial and venous pressure values. For example, a constant increase in the viscosity of the patient's blood leads to a symmetrical increase in the flow resistance in the extracorporeal circuit, as a result of which the arterial pressure drops and the venous pressure rises. By contrast, a reduction in viscosity has the opposite effect. A disadvantage is that the known alarm systems with algorithms for adaptive drift detection can avoid only those alarms that result from a relatively slow change in the arterial and/or venous pressure in the extracorporeal circuit.

EP 1 584 339 A2 describes a device for monitoring a vascular access during dialysis treatment, in which the pressure is monitored by pressure sensors both in the arterial branch and in the venous branch of the extracorporeal blood circuit. From the arterial and venous pressure, two values characteristic of the state of the vascular access are calculated in a computing unit and are then evaluated in an evaluation unit for detection of an incorrect vascular access. The known monitoring system is based on calculation of two values that are characteristic of the state of the vascular access and that are compared to two threshold values, and it is inferred that the vascular access is incorrect if both the first and second characteristic values are negative and the first characteristic value is smaller than the first threshold value and the second characteristic value is smaller than the second threshold value.

To calculate the first characteristic value, the difference between the sum of the venous and arterial pressure of a subsequent measurement and the sum of the venous and arterial pressure of a preceding measurement is determined. Whereas, in order to calculate the second characteristic value, the difference between the difference of the venous and arterial pressure of a subsequent measurement and the difference of the venous and arterial pressure of a preceding measurement is determined. These pressure differences of consecutive measurements are continuously added up. Consequently, the monitoring of the vascular access is based on the comparison of measured values of the arterial and venous pressure that have been determined in preceding and subsequent measurements. Based solely on a single measurement of the arterial and venous pressure at a certain time, a possible error state cannot be detected using the known algorithm.

DE 101 59 620 C1 discloses a means for monitoring the delivery of substitution fluid during an extracorporeal blood treatment, where, instead of monitoring the pressure in the extracorporeal blood circuit as such, a disturbance in the delivery of substitution fluid is inferred when the amplitude of the pressure waves generated by the substituate pump exceeds a predetermined threshold value.

US 2002/0190863 A1 describes a medical monitoring system in which false alarms are intended to be ruled out by using the time sequences of two measurement parameters for the evaluation.

SUMMARY OF THE INVENTION

It is an object of the present invention to make available a method for monitoring an extracorporeal blood circuit during an extracorporeal blood treatment with which the number of false alarms is reduced and which requires only minimal outlay in terms of equipment and does not require additional sensors.

A further object of the present invention is to create a device for extracorporeal blood treatment with a means for monitoring the extracorporeal blood circuit.

The method according to the present invention and the device according to the present invention are based on the fact that, during the blood treatment, the arterial pressure in the arterial branch and the venous pressure in the venous branch of the extracorporeal circuit are measured, and the sum of the arterial and venous pressure measured at the same time and the difference of the arterial and venous pressure measured at the same time are compared to predetermined limit values. The characteristic values that are compared to the predetermined limit values are therefore not values that have been calculated from the arterial and venous pressure at a preceding time and at a subsequent time. The formation of the sums and differences and the comparison with predetermined limit values is in principle sufficient for differentiating between a possible error state in the extracorporeal circuit and a false alarm that may be caused by movements of the patient and by fluctuations in viscosity and in the blood pressure of the patient.

In principle, it would also be possible for the method according to the present invention to be carried out with only one of the two characteristic values, i.e. either the sum or the difference of arterial or venous pressure. Not all false alarms could then be detected as such, but the number of false alarms could still be reduced by approximately half.

In the device according to the invention, use is made of the arterial and venous pressure sensors that are present in the known blood treatment devices. Thus, the machine adaptation for implementing the safety system is limited to simply modifying the automated evaluation of the available sensor data. Consequently, the method according to the present invention can be implemented very simply with software changes.

The predetermined limit values preferably form a limit value window with a predetermined upper limit value and a predetermined lower limit value. A possible error state is then detected if the alarm condition is satisfied, namely that both the sum of the arterial and venous pressure and the difference of the arterial and venous pressure lie outside the predetermined limit value window. If, by contrast, only the sum or the difference of the measured arterial and venous pressure is below or above the limits of the limit value window, it is assumed that a false alarm is present.

The same limit value window can in principle be used for comparing the sum of the arterial and venous pressure and the difference of the arterial and venous pressure. However, different limit value windows are preferably adopted in order to be able to adapt the alarm thresholds individually to the respective therapy requirements. The alarm windows with a width A or a width B can be set symmetrically or asymmetrically around the actual sum or difference value in a normal state.

A particularly preferred embodiment involves a further check in order to be able to detect an error state with greater certainty. A probable error state is inferred if the alarm condition is satisfied in n consecutive measurements, namely that both the sum of the arterial and venous pressure and the difference of the arterial and venous pressure lie outside the predetermined limit value windows.

The method according to the present invention and the device according to the present invention can also be combined with other methods and devices for detecting an error state in extracorporeal blood treatment. In this way, the safety of the monitoring system can be enhanced still further.

In the event of an error state, an acoustic and/or optical alarm is preferably given. In addition, the blood flow in the extracorporeal blood circuit can be interrupted in order to avoid loss of blood. In the known devices for extracorporeal blood treatment, it is possible to interrupt the blood flow by stopping the blood pump arranged in the extracorporeal circuit and/or by closing a safety valve, for example a tube clamp, arranged in the extracorporeal circuit.

Monitoring of the extracorporeal blood circuit can be effected not only in devices for hemodialysis, hemofiltration and hemodiafiltration, but also in the known cell separators in which a donor's blood is subjected to centrifugation in an extracorporeal circuit and is separated into its constituent parts.

BRIEF DESCRIPTION OF THE DRAWINGS

The method according to the invention for monitoring an extracorporeal blood circuit, and a device for extracorporeal blood treatment with a means for monitoring the extracorporeal blood circuit, are explained in more detail below on the basis of an illustrative embodiment and with reference to the drawings, in which.

DETAILED DESCRIPTION OF THE DRAWINGS

The arterial pressure and venous pressure measured in the arterial branch and venous branch of the extracorporeal blood circuit are in each case composed of the dynamic pressure in the extracorporeal circuit, generated by the flow of the blood pump, and of the dynamic pressure in the vascular access of the patient.

The dynamic pressure in the extracorporeal circuit is a function of the extracorporeal blood flow and of the sum of the flow resistances in the extracorporeal circuit. Since arterial flow resistance and venous flow resistance differ because of the differing geometry of the components through which the flow passes, the sum of the arterial pressure and venous pressure, hereinafter referred to as $P_S$, is likewise a function of the blood flow. In the known blood purification methods, the delivery rate $Q_B$ of the blood pump is generally set at a fixed value. Therefore, when the viscosity of the blood is constant, the sum of the flow resistances in the extracorporeal circuit is also constant.

The dynamic pressure in the vascular access of the patient, hereinafter referred to as the fistula pressure, is likewise a function of the blood viscosity, of the systemic blood pressure, and of the systemic vascular flow resistances. The fistula pressure is thus a patient-specific parameter and additionally depends on the nature of the vascular access, on the viscosity of the blood, and on the vessel system that supplies the vascular access with blood. In analogy to the dynamic pressure in the extracorporeal system, a change in the fistula pressure, for example caused by blood pressure fluctuations, viscosity fluctuations and positional changes on the part of the patient, lead to a change both in the arterial pressure value and the venous pressure value in the extracorporeal circuit.

Figure 1:
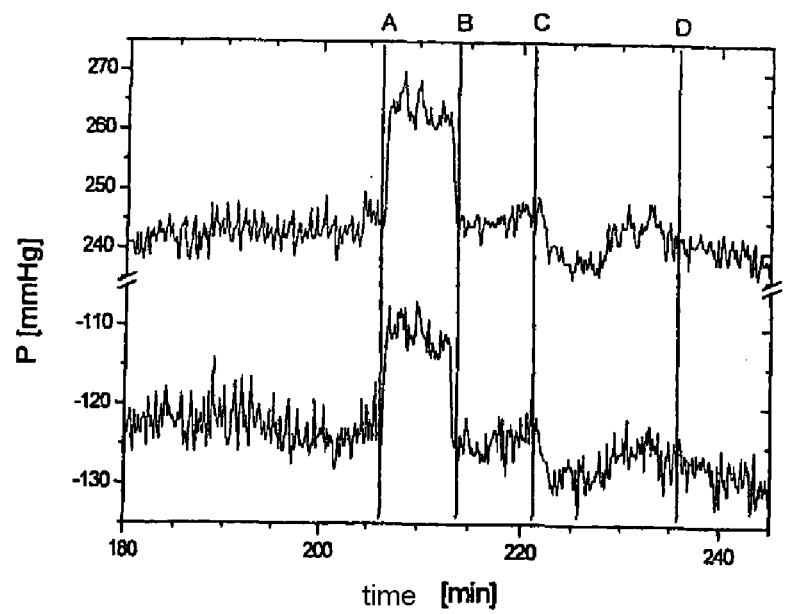
FIG. 1 shows the arterial pressure and venous pressure as a function of the treatment time during a period of movement of the patient.

FIG. 1 shows by way of example how a change in the horizontal position of the patient during a hemodialysis treatment influences the output signal of the pressure sensors provided in the arterial and venous branches of the extracorporeal circuit. In the time interval of t=206-213 minutes, the patient's bed was raised by about 20 cm. A symmetrical increase of about 15 mmHg in the arterial pressure and venous pressure due to the altered hydrostatic equilibrium conditions can clearly be seen. With an incorrect choice of the monitoring windows around the instantaneous extracorporeal pressure, this positional change, although completely safe for the patient, would lead to a false alarm if the monitoring of the extracorporeal blood circuit was based solely on comparing the arterial and/or venous pressure to predetermined limit values. In the time interval of 222-237 minutes, the output signals of the pressure sensors can be seen when the patient uses the punctured fistula arm for eating. Here too, a symmetrical change in pressure can be seen. In both cases, the difference of the arterial and venous pressure, hereinafter referred to as $\Delta P$, is constant, for which reason it is assumed that the alarm is a false alarm.

Figure 2:
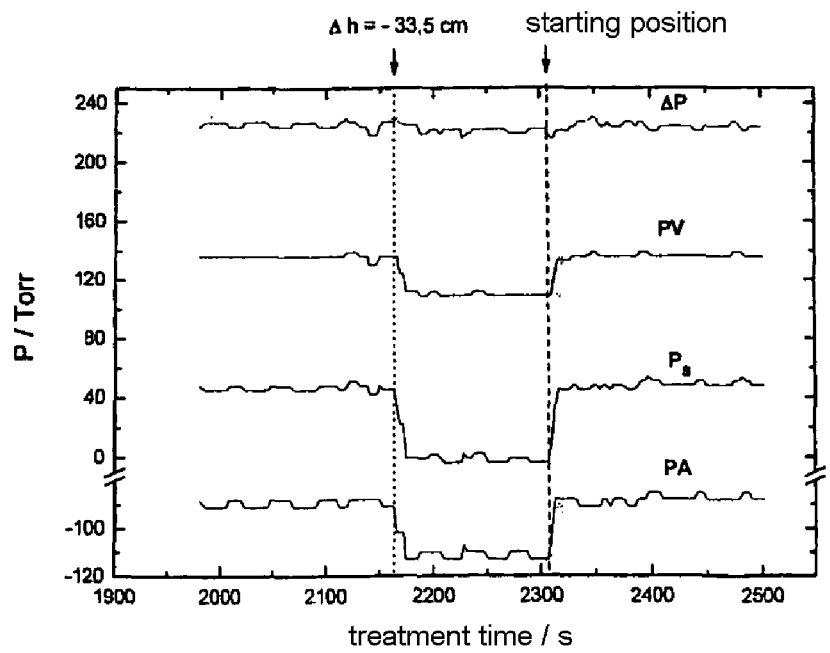
FIG. 2 shows the arterial pressure and venous pressure and the sum and difference of the arterial pressure and venous pressure as a function of the treatment time during a period of movement of the patient.

FIG. 2 shows the behavior of the arterial pressure and venous pressure at a constant effective blood flow $Q_B$ when the patient's position relative to the extracorporeal pressure sensors changes by −33.5 cm. This is the case, for example, when the patient lies down or his bed is lowered. The arterial and venous pressure values drop by the amount of the hydrostatic pressure difference, which amounts to about 0.75 torr per cm height difference between pressure sensor and fistula. The times of the positional changes are indicated by broken lines in FIG. 2. Since the arterial pressure and venous pressure in the extracorporeal circuit change by the same value in the event of a change of position of the patient, the difference $\Delta P$ remains constant. By contrast, the sum $P_S$ of the arterial pressure and venous pressure drops by twice the amount of the hydrostatic pressure difference. This behavior is seen analogously in the event of a drop in blood pressure during treatment. Here too, the arterial pressure and venous pressure in the extracorporeal circuit drop by the same amount. It is thus clearly evident that, with separate evaluation of the extracorporeal pressure signals, false alarms occur with a high degree of probability during treatment, and these false alarms can be avoided using the method according to the invention and the device according to the invention.

Figures 3, 5:
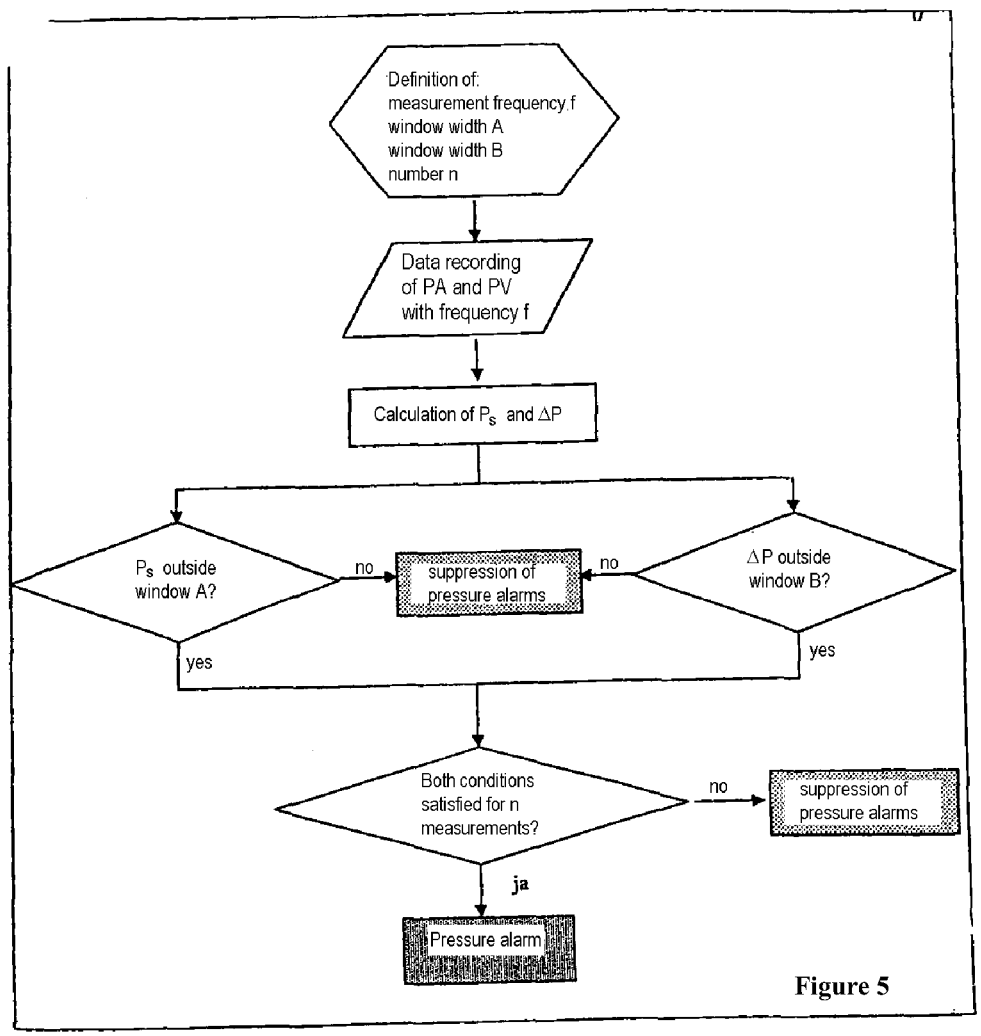
FIG. 3 shows a table illustrating the causes of false alarms.
FIG. 5 shows a flow chart describing the mode of operation of the monitoring means.

The table in FIG. 3 gives a qualitative overview of the most common causes of false alarms in the event of a change of position of the patient, a drop in blood pressure and an increase in viscosity, and it shows the trend of the arterial and venous pressure changes for the above cases.

Figure 4:
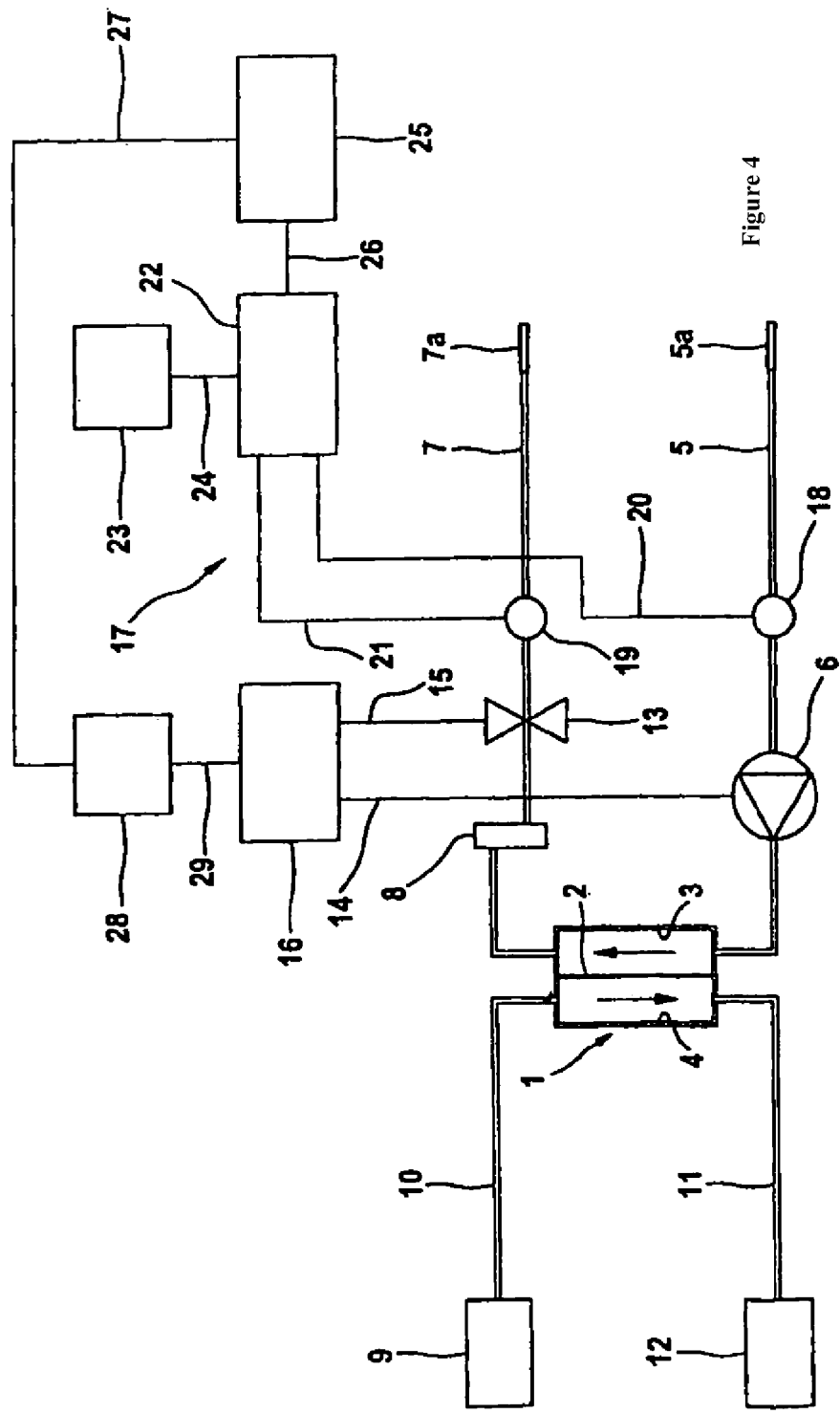
FIG. 4 shows a simplified schematic representation of an illustrative embodiment of a device for extracorporeal blood treatment, with a means for monitoring the extracorporeal blood circuit.

FIG. 4 shows a simplified schematic representation of a dialysis device with a means for monitoring the extracorporeal blood circuit, described in detail below.

The dialysis device comprises, as blood treatment means, a dialyzer 1 which is divided by a semi-permeable membrane 2 into a blood chamber 3 and a dialysis fluid chamber 4. An arterial blood conduit 5 is connected to the inlet of the blood chamber, and a peristaltic blood pump 6 is coupled into the arterial blood conduit 5. Downstream of the blood chamber 3, a venous blood conduit 7 leads from the outlet of the blood chamber to the patient. A drip chamber 8 is coupled into the venous blood conduit 7. Attached to the ends of the arterial and venous blood conduits 5, 7, there are cannulas 5a, 7a, which are pushed into a corresponding arterial or venous blood vessel, respectively, of the patient. The arterial and venous blood conduits are component parts of a tube conduit system which is designed to be disposable and which forms the extracorporeal blood circuit.

Fresh dialysis fluid is made available in a dialysis fluid source 9. From the dialysis fluid source 9, a dialysis fluid delivery line 10 leads to the inlet of the dialysis fluid chamber 4 of the dialyzer 1, while a dialysis fluid discharge line 11 leads from the outlet of the dialysis fluid chamber to a drain 12.

The dialysis device can comprise other components, for example a balance mechanism and an ultrafiltration means, etc., but these have been omitted in order to make the figure clearer.

To interrupt the blood flow, a shut-off clamp 13 is provided on the venous blood conduit 7 downstream of the drip chamber 8 and is electromagnetically actuated. The arterial blood pump 6 and the venous shut-off clamp 13 are controlled by a control unit 16 via control lines 14, 15.

The means 17 for monitoring the vascular access comprises an arterial pressure sensor 18 monitoring the pressure in the arterial blood conduit 5 and a venous pressure sensor 19 monitoring the pressure in the venous blood conduit 7. The measured values of the pressure sensors 18, 19 are transmitted to a computing unit 22 via data links 20, 21. The interim results from the calculation are stored in a memory unit 23, which is connected to the computing unit 22 via a data link 24.

To evaluate the characteristic values for the error state in the extracorporeal circuit, the monitoring means 17 comprises an evaluation unit 25 which is connected to the computing unit 22 via a data link 26. The evaluation unit 25 is connected via a control line 27 to an alarm unit 28, which is in turn connected to the control unit 16 via a control line 29.

The mode of operation of the monitoring means 17 is described in detail below with reference to FIGS. 4 and 5.

First, the parameters required for the evaluation are established. To this end, the upper and lower limit values of a first limit value window A and the upper and lower limit values of a second limit value window B are fixed. The limit values for determining the limit value windows A, B can be input manually or can be defined by the monitoring means as values stored in the memory unit 23. In addition, the number n of the measurements and the measurement frequency f are defined.

During the dialysis treatment, and by means of the pressure sensors 18, 19, the arterial pressure and venous pressure $P_{art}$, $P_{ven}$ are continuously recorded at measurement frequency f in successive cycles of in each case n consecutive measurements. In each measurement cycle, the computing unit 22 calculates, after each measurement 1, 2, 3 . . . n, the sum $P_S$ of the venous and arterial pressure and the difference $\Delta P$ between the venous and arterial pressure as measured with the pressure sensors. To calculate the sum and the difference of arterial pressure and venous pressure, the computing unit has means for forming the sum and difference. $P_S$ and $\Delta P$ are calculated according to the following equations:

$$P_S = P_{ven} + P_{art}$$

$P_{art}$: measured value of the arterial pressure in the extracorporeal circuit
$P_{ven}$: measured value of the venous pressure in the extracorporeal circuit.

$$\Delta P = P_{ven} - P_{art}$$

After each measurement 1, 2, 3 . . . n, the evaluation unit 25 checks whether $P_S$ lies within or outside the limit value window A and whether $\Delta P$ lies within or outside the limit value window B. In the case where $P_S$ or $\Delta P$ lies within the limit value window A, B, respectively, i.e. $P_S$ is smaller than the upper limit value and greater than the lower limit value of the limit value window A or $\Delta P$ is smaller than the upper limit value and greater than the lower limit value of the limit value window B, the evaluation unit 25 infers that there is no error state in the extracorporeal circuit. Accordingly, all the pressure alarms are suppressed. The sensitivity in this respect can be defined through the choice of the width of the alarm windows A and B.

In the case where $P_S$ lies outside the limit value window A and $\Delta P$ also lies outside the limit value window B, the evaluation unit 25 infers that there is a possible error state in the extracorporeal circuit.

However, in order to reduce the susceptibility of the protective system to faults, for example in the event of brief artificial pressure fluctuations, it is not just one measurement in a measurement cycle that is used for the evaluation, but instead n consecutive measurements.

During the blood treatment, the monitoring means 17 performs, in successive steps, n consecutive measurements with a frequency f, for measuring the arterial pressure and venous pressure. In the case where, for n measurements, both $P_S$ and $\Delta P$ lie outside the respective limit value window A, B, the evaluation unit 25 infers that the possible error state is a probable error state in the extracorporeal circuit. If both conditions are satisfied for n consecutive measurements, the evaluation unit 25 therefore sends an alarm signal via the control line 27 to the alarm unit 28, which emits an acoustic and/or optical alarm.

The alarm unit 28 also sends an alarm signal via the control line 29 to the control unit 16, which thereupon stops the blood pump 6 and closes the venous shut-off clamp 13.

During the blood treatment, the monitoring means 17 performs, in successive steps, n consecutive measurements with a frequency f, for measuring the arterial pressure and venous pressure. In the case where, for n measurements, both P.sub.S and .DELTA.P lie outside the respective limit value window A, B, the evaluation unit 25 infers that the possible error state is a probable error state in the extracorporeal circuit. If both conditions are satisfied for n consecutive measurements, the evaluation unit 25 therefore sends an alarm signal via the control line 27 to the alarm unit 28, which emits an acoustic and/or optical alarm. The alarm unit can comprise an acoustic emitter, an optical emitter, or both.

The invention claimed is:

1. A device for detecting an error state in extracorporeal blood treatment, comprising:
    an extracorporeal blood circuit comprising an arterial blood conduit connected to an inlet of a blood treatment device and to an arterial attachment for a vascular access, and a venous blood conduit connected to an outlet of the blood treatment device and to a venous attachment for the vascular access;
    an arterial pressure sensor for measuring the pressure in the arterial blood conduit;
    a venous pressure sensor for measuring the pressure in the venous blood conduit;
    a monitoring means comprising a computing unit and a memory unit, the computing unit being configured for receiving pressure values measured by the arterial pressure sensor and venous pressure sensor, wherein the pressure values are transmitted to the computing unit via data links, and wherein the computing unit is programmed to calculate both a sum ($P_s$) of the values of arterial pressure and venous pressure measured at time $t_n$, and a difference ($\Delta P$) of the values of the arterial pressure and venous pressure measured at time $t_n$, the memory unit being connected to the computing unit via a data link and having stored therein a predetermined limit value window A and a predetermined limit value window B, the monitoring means being programmed to continuously compare both the sum $P_s$ at time $t_n$ to the predetermined limit value window A, and the difference $\Delta P$ at time $t_n$ to the predetermined limit value window B throughout the duration of the extracorporeal blood treatment, to evaluate $P_s$ and $\Delta P$ at a number of times, and wherein a first alarm condition is determined to be present if both $P_s$ and $\Delta P$ lie outside the respective predetermined limit value windows; and an alarm unit connected to the computing unit via a control line, wherein the alarm unit comprises an acoustic emitter, an optical emitter, or both, and emits an alarm if an error state is detected, wherein the error state is detected if a first alarm condition is present a predetermined number of times.

2. The device of claim 1, wherein the respective predetermined limit value windows each have a fixed upper limit value and a fixed lower limit value; and the monitoring means further being programmed to compare $P_s$ to the upper limit value and the lower limit value of the predetermined limit value window A, and being programmed to compare $\Delta P$ to the upper limit value and the lower limit value of the predetermined limit value window B.

3. The device of claim 1, wherein the monitoring means is programmed to evaluate $P_s$ and $\Delta P$ at a predetermined number of consecutive times (n), and detect an error state if the first alarm condition is present for n consecutive times.

4. The device of claim 3, further comprising at least one of a stoppable blood pump arranged in the extracorporeal blood circuit and a closable safety valve arranged in the extracorporeal blood circuit for interrupting the blood flow in the extracorporeal blood circuit if the error state is detected.

5. The device of claim 3, further comprising a stoppable blood pump arranged in the extracorporeal blood circuit and a closable safety valve arranged in the extracorporeal blood circuit for interrupting the blood flow in the extracorporeal blood circuit if the error state is detected, wherein the alarm unit is configured to send an alarm signal to stop the blood pump and close the safety valve if the error state is detected.

* * * * *